US005655538A

United States Patent [19]

Lorraine et al.

[11] Patent Number: 5,655,538

[45] Date of Patent: Aug. 12, 1997

[54] ULTRASONIC PHASED ARRAY TRANSDUCER WITH AN ULTRALOW IMPEDANCE BACKFILL AND A METHOD FOR MAKING

[75] Inventors: Peter William Lorraine; Lowell Scott Smith, both of Niskayuna, N.Y.

[73] Assignee: General Electric Company, Schenectady, N.Y.

[21] Appl. No.: 491,208

[22] Filed: Jun. 19, 1995

[51] Int. Cl.[6] ................................ A61B 8/00; H01L 41/22

[52] U.S. Cl. ...................................... 128/662.03; 29/25.35

[58] Field of Search ........................ 128/662.03; 310/334, 310/336; 29/25.35

[56] References Cited

U.S. PATENT DOCUMENTS

| | | | |
|---|---|---|---|
| 4,442,715 | 4/1984 | Brisken et al. | 73/626 |
| 4,528,652 | 7/1985 | Horner et al. | 310/327 X |
| 4,734,963 | 4/1988 | Ishiyama | 29/25.35 |
| 4,779,244 | 10/1988 | Horner et al. | 367/140 |
| 5,039,774 | 8/1991 | Shikinami et al. | 128/662.03 |
| 5,311,095 | 5/1994 | Smith et al. | 310/334 |

OTHER PUBLICATIONS

"Two–Dimensional Array Tranducers Using Hybrid Transducers Using Hybrid Connection Technology", by S. Smith, et al, Dept. of Biomedical Engineering, Duke University, Durham, NC 27706 (4 pages).

"Modified SiO2 Aerogels as Acoustic Impedance Matching Layers In Ultrasonic Devices" by R. Gerlach, et al, Journal of Non–Crystalline Solids 145, pp. 227–232.

"Elastic Nonlineartity of Aerogels" by J. Gross, et al, Physical Review B, vol. 45, No. 22, 1 Jun. 1992–II, pp. 12774–12777.

"Matrix Array Transducer and Flexible Matrix Array Transducer" by T. Kojima, 1986 Ultrasonics Symposium, pp. 649–654.

"Hybrid Linear and Matrix Acoustic Arrays" by M. Pappalardo, Ultrasonics, Mar. 1981, pp. 81–86.

"Two Dimensional Arrays for Medical Ultrasound" by S. Smith, et al, Ultrasonic Imaging 14, pp. 214–233, 1992.

*Primary Examiner*—Francis Jaworski

*Attorney, Agent, or Firm*—David C. Goldman; Marvin Snyder

[57] ABSTRACT

The present invention discloses an ultrasonic phased array transducer with an ultralow backfill and a method for making. The ultrasonic phased array includes a low density backfill material having an ultralow acoustic impedance. The backfill material is either an aerogel, a carbon aerogel, an xerogel, or a carbon xerogel. A piezoelectric ceramic material and two matching layers are bonded to the backfill material. In one embodiment, a plurality of interconnect vias are formed in the backfill material with conducting material deposited in the vias. A portion of the bonded matching layers, the piezoelectric ceramic material, and the backfill material have isolation cuts therethrough to form an array of electrically and acoustically isolated individual elements. In a second embodiment, the backfill material is bonded to an electronic layer at a face opposite to the piezoelectric ceramic material and the matching layers. Then isolation cuts are made through the matching layers, the piezoelectric ceramic material, and the backfill material, to form an array of electrically and acoustically isolated individual elements.

19 Claims, 7 Drawing Sheets

FIG. 1
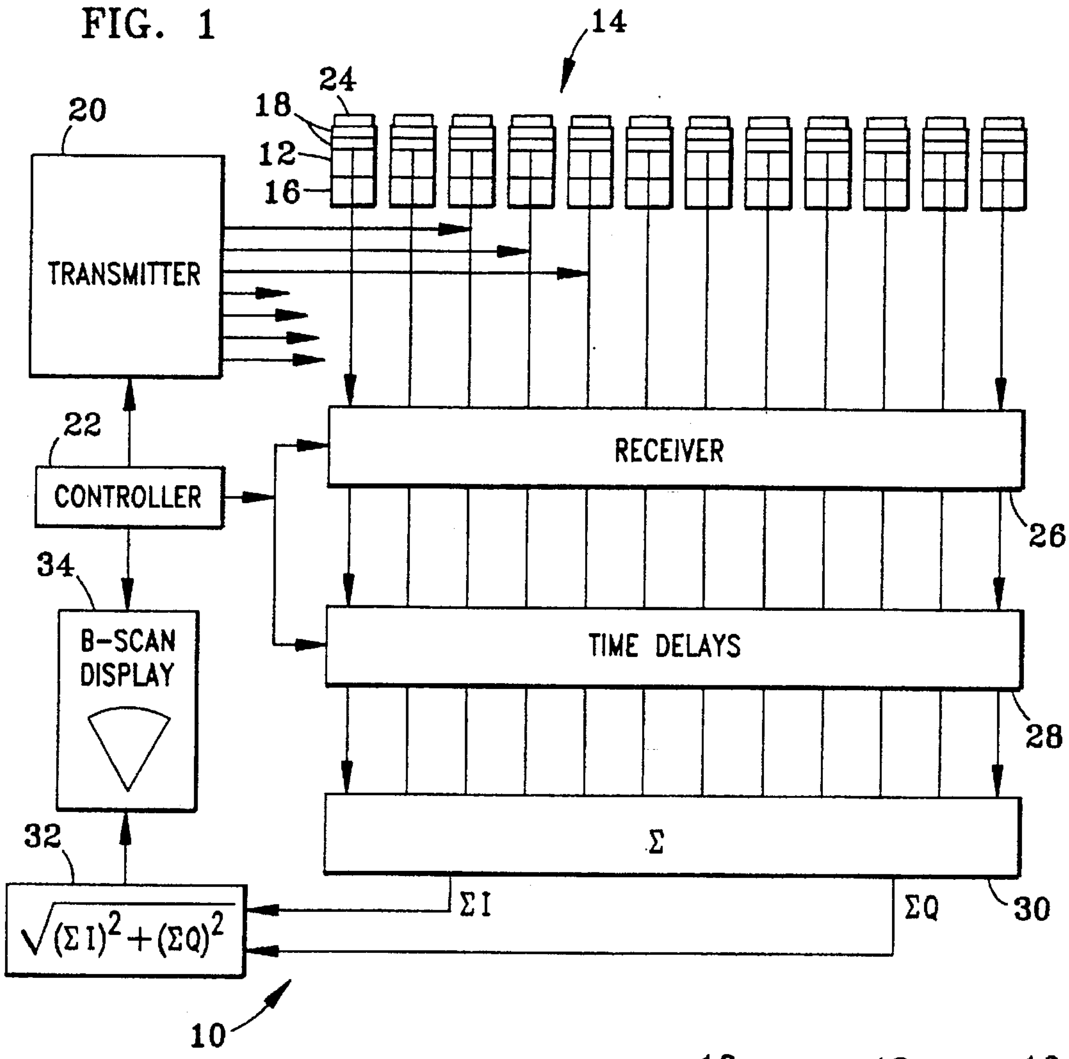
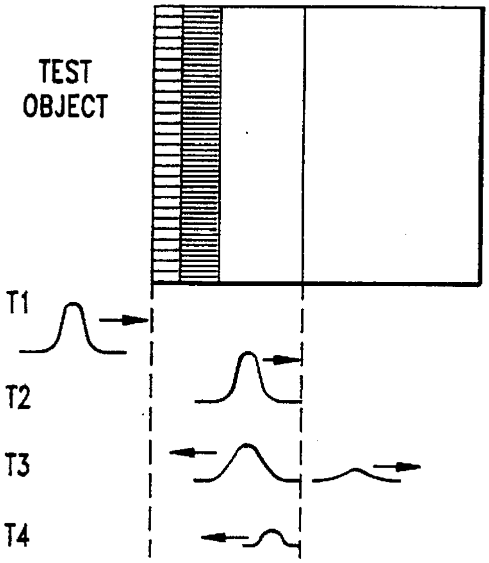
FIG. 2A
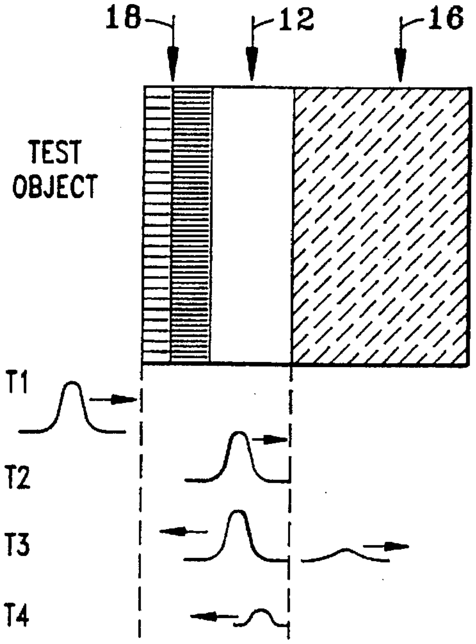
FIG. 2B

ULTRASONIC PHASED ARRAY TRANSDUCER WITH AN ULTRALOW IMPEDANCE BACKFILL AND A METHOD FOR MAKING

BACKGROUND OF THE INVENTION

The present invention relates generally to an ultrasonic phased array transducer and more particularly to an ultrasonic phased array transducer having an ultralow impedance backfill and a method for making.

A typical ultrasonic phased array transducer used in medical and industrial applications includes one or more piezoelectric elements placed between a pair of electrodes. The electrodes are connected to a voltage source. When a voltage is applied, the piezoelectric elements are excited at a frequency corresponding to the applied voltage. As a result, the piezoelectric element emits an ultrasonic beam of energy into a media that it is coupled to at frequencies corresponding to the convolution of the transducer's electrical/acoustical transfer function and the excitation pulse. Conversely, when an echo of the ultrasonic beam strikes the piezoelectric elements, each element produces a corresponding voltage across its electrodes.

In addition, the ultrasonic phased array typically includes acoustic matching layers coupled to the piezoelectric elements. The acoustic matching layers transform the acoustic impedance of the patient or object to a value closer to that of the piezoelectric element. This improves the efficiency of sound transmission to the patient/object and increases the bandwidth over which sound energy is transmitted. Also, the ultrasonic phased array includes an acoustic backing layer (i.e., a backfill) coupled to the piezoelectric elements opposite to the acoustic matching layers. The backfill has a lower impedance than the piezoelectric elements in order to direct more of the ultrasonic beam towards the patient/object rather than the backfill. Typically, the backfill is made from a thick, lossy material that provides high attenuation for diminishing reverberations of the sound frequencies involved. As an echo of sound waves goes to or returns from the patient/object some of the waves will escape into the backfill material and may interfere with other echoes returning from the patient/object. However, most of these sound waves are attenuated greatly by the thick, lossy, backfill material so that returned echoes from the backfill are unimportant.

However, a problem with using a thick, lossy, backfill with an ultrasonic phased array transducer is that it is difficult to achieve electrical and acoustical isolation by separating the array of piezoelectric elements with independent electrical connections. Typically, the piezoelectric elements are separated by using a dicing saw, a kerf saw, or by laser machining. Electrical connections made through the backfill layer must not interfere with the other acoustic properties (i.e. high isolation, high attenuation, and backfill impedance). In certain applications such as 1.5 or 2 dimensional arrays, there is a very small profile which makes it extremely difficult to make electrical connections without interfering with the acoustic properties of the ultrasonic phased array.

One approach that has been used to overcome this interconnect problem is to bond wires or flexible circuit boards to the piezoelectric elements. However, these schemes are difficult to implement with very small piezoelectric elements or in 2 dimensional (2-D) arrays, since backfill properties or acoustic isolation may be compromised. An example of a handwiring scheme that is not practicable for commercial manufacturing is disclosed in Kojima, *Matrix Array Transducer* and *Flexible Matrix Array Transducer*, IEEE ULTRASONICS, 1986, pp. 649–654. An example of another scheme that has been disclosed in Pappalardo, *Hybrid Linear* and *Matrix Acoustic Arrays*, ULTRASONICS, March 1981, pp. 81–86, is to stack individual lines of arrays of piezoelectric elements including the backfill. However, the scheme disclosed in Pappalardo is deficient because there is poor dimensional control. In Smith et al., *Two Dimensional Arrays for Medical Ultrasound*, ULTRASONIC IMAGING, vol. 14, pp. 213–233 (1992), a scheme has been disclosed which uses epoxy wiring guides with conducting epoxy and wire conductors. However, the scheme disclosed in Smith et al. is deficient because it suffers from poor manufacturability and acoustic properties. Also, a three dimensional (3-D) ceramic interconnect structure based multi-layer ceramic technology developed for semiconductor integrated circuits has been disclosed in Smith et al., *Two Dimensional Array Transducer Using Hybrid Connection Technology*, IEEE ULTRASONICS SYMPOSIUM, 1992, pp. 555–558. This scheme also suffers from poor manufacturability and acoustic properties.

Thus, there is a need for a backfill that can be used in an ultrasonic phased array transducer such that electrical and acoustical isolation of the array of piezoelectric elements can be maintained without interfering with their electrical and acoustical properties.

SUMMARY OF THE INVENTION

Therefore, it is a primary objective of the present invention to provide an ultrasonic phased array transducer having a backfill with an ultralow impedance that is made from aerogels, carbon aerogels, xerogels, or carbon xerogels, eliminating the need for a thick, lossy, backfill.

A second object of the present invention is to provide an ultrasonic phased array transducer with a backfill that can be electrically and acoustically isolated without interfering with the electrical and acoustical properties of the array.

Thus, in accordance with the present invention, there is provided an ultrasonic phased array transducer and a method for making. In the present invention, a low density backfill material having an ultralow acoustic impedance is bonded to a piezoelectric ceramic material and a plurality of matching layers. Portions of the bonded plurality of matching layers, the piezoelectric ceramic material, and the backfill material are cut therethrough to form an array of electrically and acoustically isolated individual elements.

In accordance with a first embodiment of the present invention, there is provided an ultrasonic phased array transducer and a method for making. In the first embodiment, there is a low density backfill material having an ultralow acoustic impedance. A flexible circuit board is bonded at one end of the ultralow impedance backfill. A piezoelectric ceramic material and a plurality of matching layers are bonded to the flexible circuit board and the backfill material, wherein the flexible circuit board is bonded between the backfill material and the piezoelectric ceramic material. A portion of the bonded plurality of matching layers, the piezoelectric ceramic material, the flexible circuit board, and the backfill material are cut to form an array of electrically and acoustically isolated individual elements.

In accordance with a second embodiment of the present invention, there is provided an ultrasonic phased array transducer and a method for making. In the second embodiment, there is a low density backfill material having an ultralow acoustic impedance. A piezoelectric ceramic material and a plurality of matching layers are bonded to the backfill material. A plurality of interconnect vias are formed in the backfill material. A conducting material is then deposited in the plurality of interconnect vias. Portions of the bonded plurality of matching layers, the piezoelectric ceramic material, and the backfill material are cut to form an array of electrically and acoustically isolated individual elements.

In accordance with another embodiment of the present invention, there is provided an ultrasonic phased array transducer and a method for making. In the third embodiment, there is an electrically conductive low density backfill material having an ultralow acoustic impedance. A piezoelectric ceramic material and a plurality of matching layers are bonded to the backfill material. An electronic layer is bonded to the backfill material at a face opposite to the bonded piezoelectric ceramic material and plurality of matching layers. The electronic layer is used for making electrical contacts to the piezoelectric ceramic material and to external devices. Portions of the bonded plurality of matching layers, the piezoelectric ceramic material, and the backfill material are cut to form an array of electrically and acoustically isolated individual elements.

In accordance with still another embodiment of the present invention, there is provided an ultrasonic phased array transducer and a method for making. In the fourth embodiment, a piezoelectric ceramic material and a plurality of matching layers are bonded on a substrate. The bonded plurality of matching layers and the piezoelectric ceramic material are cut to form an array of electrically and acoustically isolated individual elements. A low density backfill material having an ultralow acoustic impedance is deposited over the array of electrically and acoustically isolated individual elements. Next, a plurality of interconnect vias are formed in the backfill material and deposited with a conducting material in the plurality of interconnect vias.

While the present invention will hereinafter be described in connection with an illustrative embodiment and method of use, it will be understood that it is not intended to limit the invention to this embodiment. Instead, it is intended to cover all alternatives, modifications and equivalents as may be included within the spirit and scope of the present invention as defined by the appended claims.

BRIEF DESCRIPTION OF THE DRAWINGS

FIG. 1 is a schematic of an ultrasonic phased array transducer and associated transmitter/receiver electronics used with the present invention;

FIGS. 2A–2B are schematics showing a sound echo returning from an object to a conventional ultrasonic phased array having a lossy backing and to an ultrasonic phased array having an ultralow backing according to the present invention, respectively;

DETAILED DESCRIPTION OF THE PRESENT INVENTION

Figure 3:
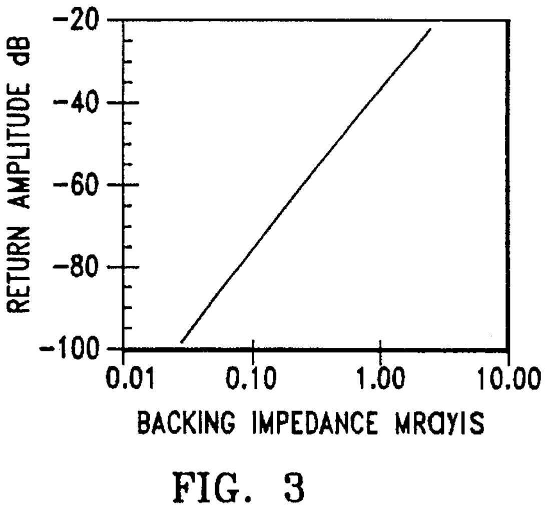
FIG. 3 is a plot showing return echo amplitude as a function of backing impedance.

FIG. 1 is a schematic of an ultrasonic phased array imager 10 which is used in medical and industrial applications. The imager 10 includes a plurality of piezoelectric elements 12 defining a phased array 14. The piezoelectric elements are preferably made from a piezoelectric material such as lead zirconium titanate (PZT) or a relaxor material such as lead magnesium niobate titanate and are separated to prevent cross-talk and have an isolation in excess of 20 decibels. A backfill layer 16 is coupled at one end of the phased array 14. The backfill layer 16 has a low density and an ultralow impedance for preventing ultrasonic energy from being transmitted or reflected from behind the piezoelectric elements 12 of the phased array 14. Acoustic matching layers 18 are coupled to an end of the phased array 14 opposite from the backfill layer 16. The matching layers 18 provide suitable matching impedance to the ultrasonic energy as it passes between the piezoelectric elements 12 of the phased array 14 and the patient/object. In the illustrative embodiment, there are two matching layers preferably made from a polymer having an acoustic impedance ranging from about 1.8 MRayls to about 2.5 MRayls and a composite material having an acoustic impedance ranging from about 6 MRayls to about 12 MRayls.

A transmitter 20 controlled by a controller 22 applies a voltage to the plurality of piezoelectric elements 12 of the phased array 14. A beam of ultrasonic energy is generated and propagated along an axis through the matching layers 18 and a lens 24. The matching layers 18 broaden the bandwidth (i.e., damping the beam quickly) of the beam and the lens 24 directs the beam to a patient/object. The backfill layer 16 prevents the ultrasonic energy from being transmitted or reflected from behind the piezoelectric elements 12 of the phased array 14. Echoes of the ultrasonic beam energy return from the patient/object, propagating through the lens 24 and the matching layers 18 to the PZT material of the piezoelectric elements 12. The echoes arrive at various time delays that are proportional to the distances from the ultrasonic phased array 14 to the patient/object causing the echoes. As the echoes of ultrasonic beam energy strike the piezoelectric elements, a voltage signal is generated and sent to a receiver 26. The voltage signals at the receiver 26 are delayed by an appropriate time delay at a time delay means 28 set by the controller 22. The delay signals are then summed at a summer 30 and a circuit 32. By appropriately selecting the delay times for all of the individual piezoelectric elements and summing the result, a coherent beam sum is formed. The coherent beam sum is then displayed on a B-scan display 34 that is controlled by the controller 22. A more detailed description of the electronics connected to the phased array is provided in U.S. Pat. No. 4,442,715, which is incorporated herein by reference.

As mentioned above, conventional backfill materials are made from a thick, lossy backing to provide high attenuation for echoes of sound waves returning from the patient/object towards the transducer. FIG. 2A is a schematic showing a sound echo returning from an object to a conventional ultrasonic phased array having a thick, lossy backing. In FIG. 2A, a sound echo pulse returns from an object to the matching layers at time $T_1$. At $T_2$, which is greater than $T_1$, the sound echo pulse reaches the interface of the piezoelectric ceramic material and the lossy backfill. A portion of the pulse propagates into the lossy backfill and a diminished pulse is reflected back at $T_3$, which is greater than $T_2$. Subsequently, the sound in the backfill will reflect off the back surface of the backfill. In a backfill without loss, this reflected sound propagates through the backfill and will be partially transmitted back into the piezoelectric material as an unwanted signal at time $T_4$. For this reason, the conventional backfills need high attenuation to reduce the unwanted signals to harmless levels. On the other hand, in FIG. 2B, which shows a schematic of a sound echo returning from an object towards the ultrasonic phased array 14 having an ultralow backfill 16, the amount of energy that escapes into the backfill is significantly diminished and the reflected pulse at $T_3$ is greater. Since the pulse that escapes into the backfill 16 is so much smaller, reverberations from the backfill are diminished. This concept is further illustrated in FIG. 3 which shows a plot of return echo amplitude after reflection from the back surface of the backfill as a function of backfill impedance. The backfill impedance for the highly attenuating conventional backfill of FIG. 2A has an impedance which is typically greater than 2.5 MRayl and returns an amplitude of approximately −20 dB. However, the backfill impedance for the ultralow backfill 16 of the present invention has an impedance which is substantially less than 1.0 MRayl and returns an amplitude of approximately −60 dB.

Figure 4:
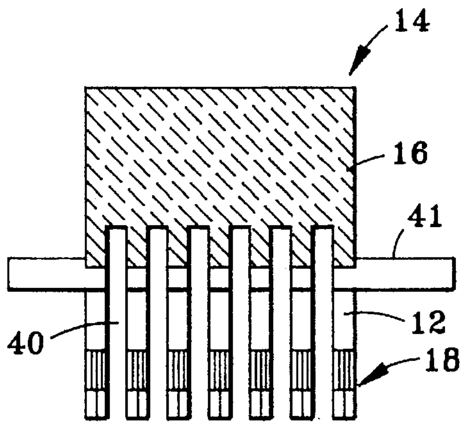
FIG. 4 is a schematic showing the ultrasonic phased array transducer with ultralow backing in a first embodiment.

FIG. 4 is a schematic showing the ultrasonic phased array transducer and the backfill material 16 in more detail according to a first embodiment which is directed to a stack of elements in one direction. The ultrasonic phased array 14 includes a low density backfill material 16 having an ultralow acoustic impedance made from either an aerogel or an xerogel. A thin film of a flexible printed circuit board 41 is bonded to one side of the backfill material 16. A piezoelectric ceramic material 12 and two matching layers 18 are bonded to the flexible printed circuit board 41 and the backfill material 16, wherein the flexible printed circuit board is placed between the piezoelectric ceramic material and the backfill material. A portion of the bonded matching layers 18, the piezoelectric ceramic material 12, the flexible printed circuit board 41 and the backfill material 16 have isolation cuts 40 therethrough to form an array of electrically and acoustically isolated individual elements.

Figure 5A:
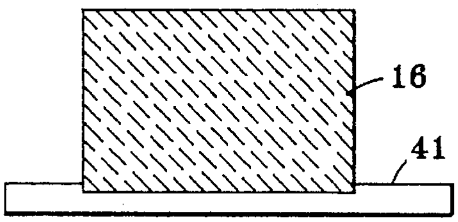
FIGS. 5A–5C illustrate a schematic method of forming the ultrasonic phased array transducer according to the first embodiment.
Figure 5B:
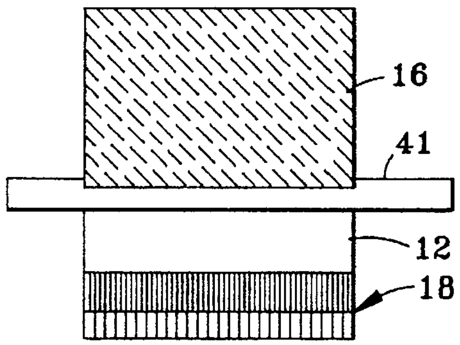
Figure 5C:
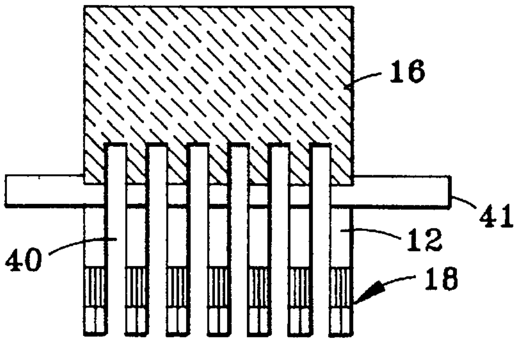

FIGS. 5A–5C illustrate a schematic method of forming the ultrasonic phased array transducer according to the first embodiment. The specific processing conditions and dimensions serve to illustrate the present method but can be varied depending upon the materials used and the desired application and geometry of the phased array transducer. First, as shown in FIG. 5A, a slab of low density backfill material 16 such as an organic or inorganic aerogel or xerogel is bonded to a flexible printed circuit board 41. The aerogel or xerogel backfill material 16 has a density of 0.02–0.2 $gm.cm^{-3}$ and an acoustic impedance that is substantially less than 1.0 MRayl and an acoustic impedance in the illustrative embodiment that is less than 0.5 MRayl, preferably between 0.01–0.4 MRayls. Once the aerogel or xerogel backfill material 16 has been bonded to the flexible printed circuit board 41, a piezoelectric ceramic material 12 and two matching layers 18 are bonded to the flexible printed circuit board and the backfill material in FIG. 5B, so that the printed circuit board is placed between the backfill and the piezoelectric. In FIG. 5C, a plurality of isolation cuts 40 are cut through a portion of the matching layers 18, the piezoelectric ceramic material 12, the flexible printed circuit board 41, and the backfill material 16 by a laser or a dicing saw to form an array of electrically and acoustically isolated individual elements.

Figure 6:
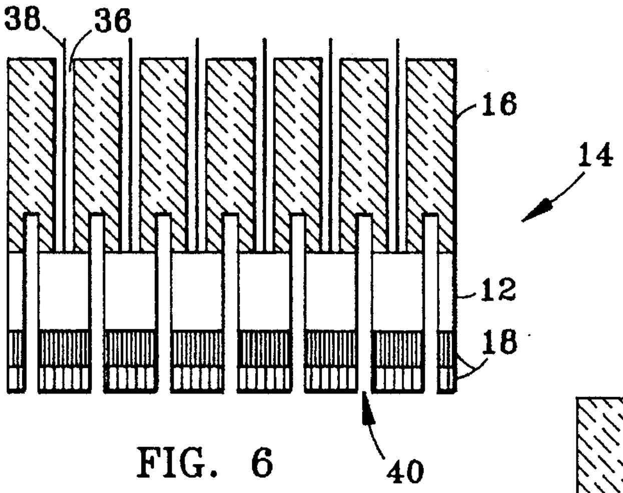
FIG. 6 is a schematic showing the ultrasonic phased array transducer with ultralow backing in a second embodiment.

FIG. 6 is a schematic showing the ultrasonic phased array transducer and the backfill material 16 in more detail according to a second embodiment, which is directed to a 1.5 dimensional or 2-D array. The ultrasonic phased array 14 includes a low density backfill material 16 having an ultralow acoustic impedance made from either an aerogel or an xerogel. A piezoelectric ceramic material 12 and two matching layers 18 are bonded to the backfill material. A plurality of interconnect vias(i.e., holes) 36 are formed in the backfill material 16 and each have a conducting material 38 deposited therein. A portion of the bonded matching layers 18, the piezoelectric ceramic material 12, and the backfill material 16 in the front face have isolation cuts 40 therethrough to form an array of electrically and acoustically isolated individual elements. In addition, the ultrasonic phased array transducer 14 may include solder pads patterned on the backfill 16 for connecting various types of electronics such as cables, flexible circuit boards, or integrated circuits.

Figure 7A:
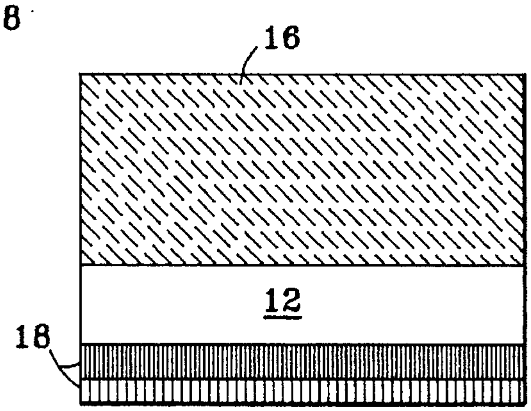
FIGS. 7A–7D illustrate a schematic method of forming the ultrasonic phased array transducer according to the second embodiment.

FIGS. 7A–7D illustrate a schematic method of forming the ultrasonic phased array transducer according to the second embodiment. The specific processing conditions and dimensions serve to illustrate the present method but can be varied depending upon the materials used and the desired application and geometry of the phased array transducer. First, as shown in FIG. 7A, a slab of low density backfill material 16 such as an organic or inorganic aerogel or xerogel is bonded to a piezoelectric ceramic material 12 and to two matching layers 18. The aerogel or xerogel backfill material 16 has a density of 0.02–0.2 $gm.cm^{-3}$ and an acoustic impedance that is substantially less than 1.0 MRayl and an acoustic impedance in the illustrative embodiment that is less than 0.5 MRayl, preferably between 0.01–0.4 MRayls. Once the aerogel or xerogel backfill material 16 has been bonded to the piezoelectric ceramic material 12 and to the matching layers 18 at a depth of a few millimeters, the bonded structure is then planarized.

Figure 7B:
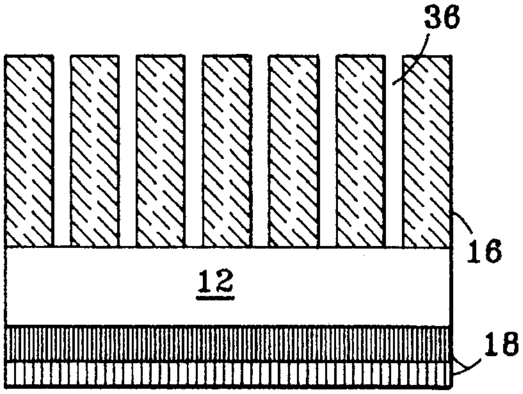

Next, in FIG. 7B, a plurality of interconnect vias 36 are formed in the backfill material 16 by laser machining. Since the backfill material 16 has less than 0.1 the density of the piezoelectric ceramic material and the matching layers, much less material needs to be removed and thus the effective thickness of the material is reduced. Thus, narrow via holes 36 may be machined quickly and deeply through the low density backfill material 16.

Figure 7C:
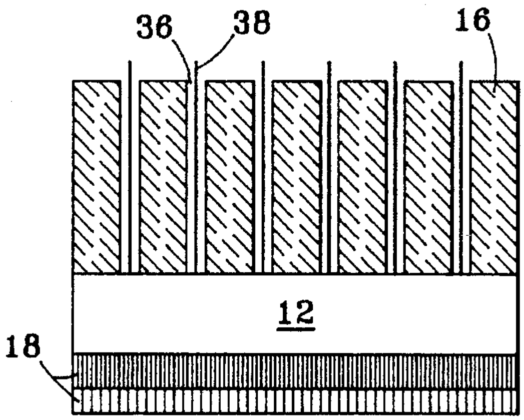
Figure 7D:
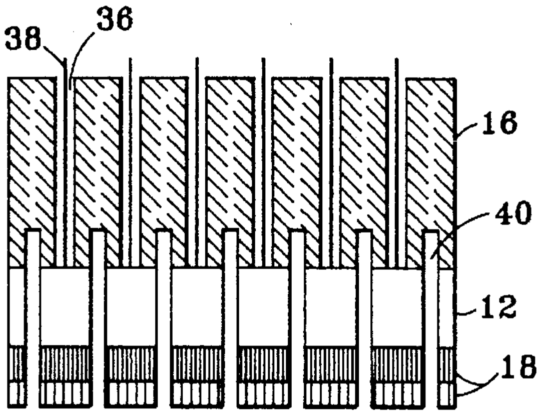

After the plurality of via holes have been machined, a conducting material 38 is deposited in each of the plurality of interconnect vias in FIG. 7C. The conducting material is deposited in each of the vias by flowing, electrodeless chemical deposition, chemical vapor deposition, or by electroplating. In the present invention, the conducting material may be deposited metal such as copper, silver, gold, or a polymer. In FIG. 7D, a plurality of isolation cuts 40 are cut through a portion of the matching layers 18, the piezoelectric ceramic material 12, and the backfill material 16 by a laser or a dicing saw to form an array of electrically and acoustically isolated individual elements.

Figure 8A:
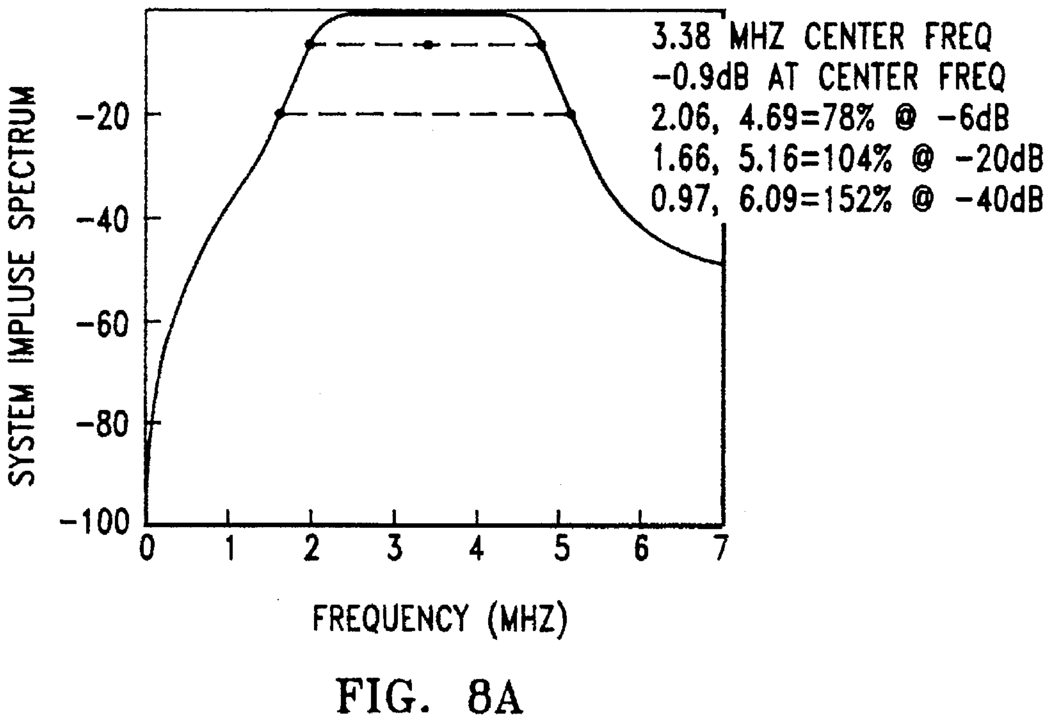
FIGS. 8A–8B show the impulse spectrum and impulse response for a conventional ultrasonic phased array having a lossy backing, respectively.
Figure 8B:
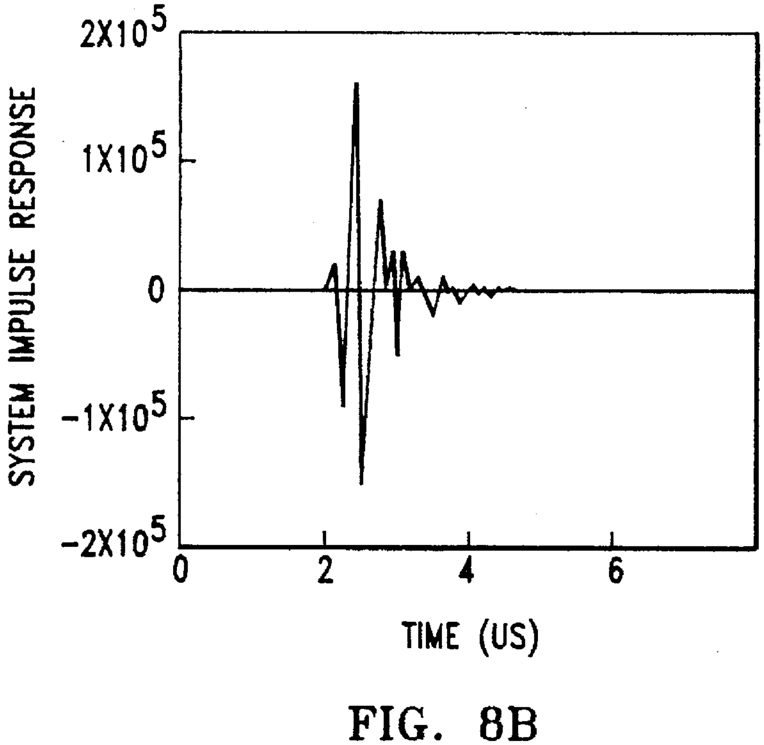
Figure 9A:
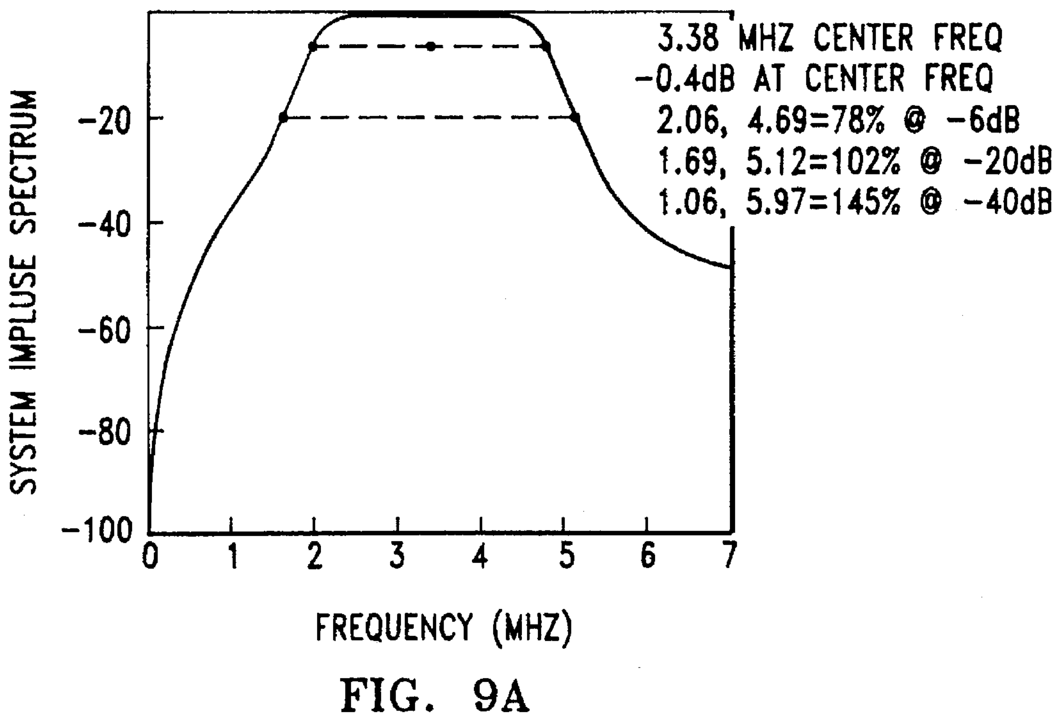
FIGS. 9A–9B show the impulse spectrum and impulse response for an ultrasonic phased array having an ultralow backing according to the present invention, respectively.
Figure 9B:
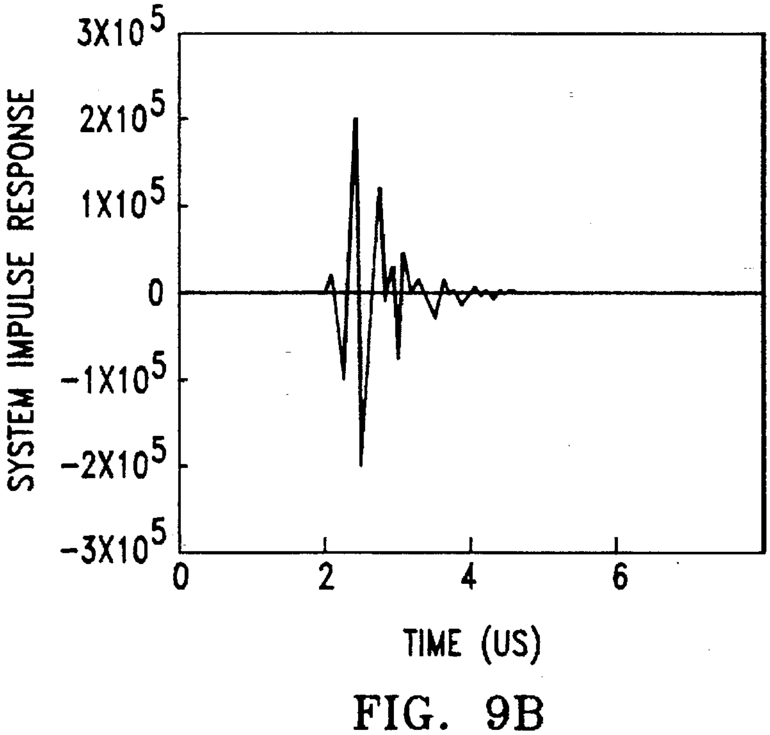

The ultrasonic phased array transducer produced from the method shown in FIGS. 7A–7D has a significant sensitivity increase as compared to the conventional ultrasonic phased array having a lossy backing. For example, FIGS. 8A–8B show that the impulse spectrum and impulse response for a conventional ultrasonic phased array having a lossy backing, respectively, is lower because more of the sound is attenuated in the backing. However, since the backfill material of the present invention has an ultralow impedance, the sound sensitivity is greater. In particular, FIGS. 9A–9B show that the impulse spectrum and impulse response for the ultrasonic phased array having an ultralow impedance backing (Z=0.05 MRayls) according to the present invention, respectively, has a sensitivity increase of about 2 dB.

Figure 10:
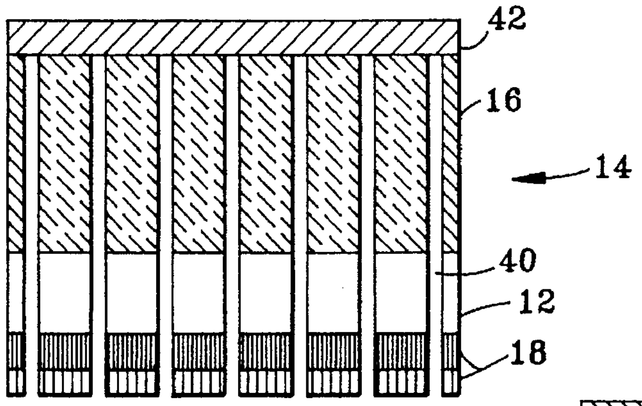
FIG. 10 is a schematic showing the ultrasonic phased array transducer in a third embodiment.

A third embodiment of the ultrasonic phased array transducer is shown in the schematic of FIG. 10. Unlike the first and second embodiments, the ultrasonic phased array transducer of the third embodiment includes a low density electrically conductive backfill material 16 having an ultralow acoustic impedance such as carbon aerogel or a carbon xerogel. A piezoelectric ceramic material 12 and two matching layers 18 are bonded to the backfill material. In addition, the backfill material 16 is bonded to an electronic layer 42 at a face opposite to the piezoelectric ceramic material 12 and the matching layers 18. The electronic layer is used to make electrical contacts to the piezoelectric ceramic material and to external devices. A portion of the bonded matching layers 18, the piezoelectric ceramic material 12, and the backfill material 16 in the front face have isolation cuts 40 therethrough to form an array of electrically and acoustically isolated individual elements. In addition, the ultrasonic phased array transducer 14 may include solder pads patterned on the backfill 16 for connecting various types of electronics such as cables, flexible circuit boards, or integrated circuits.

Figure 11A:
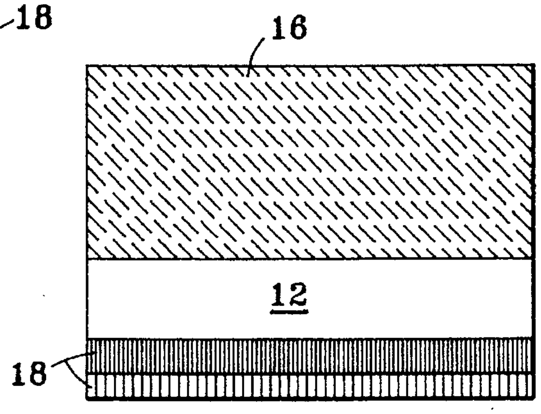
FIGS. 11A–11C illustrate a schematic method of forming the ultrasonic phased array transducer according to the third embodiment.
Figure 11B:
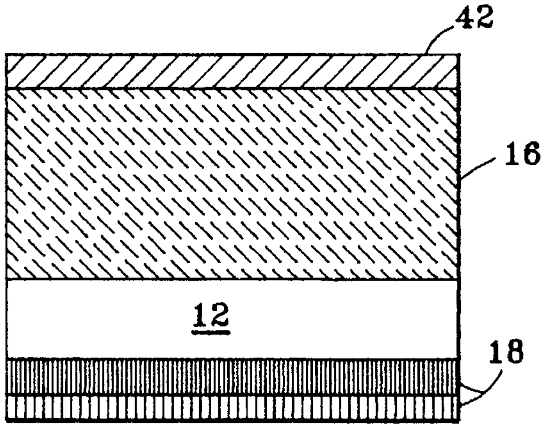
Figure 11C:
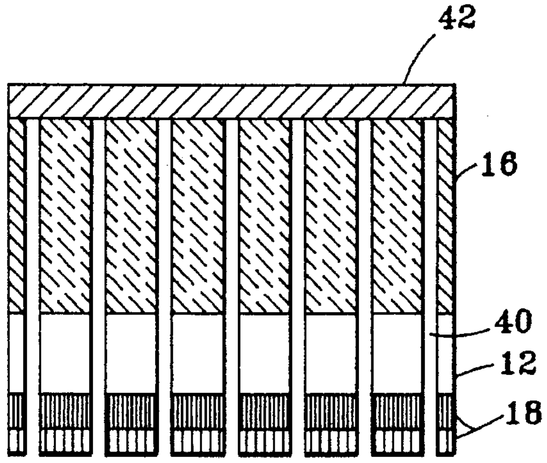

FIGS. 11A–11C illustrate a schematic method of forming the ultrasonic phased array transducer according to the third embodiment. The specific processing conditions and dimensions serve to illustrate the present method but can be varied depending upon the materials used and the desired application and geometry of the phased array transducer. First, as shown in FIG. 11A, a slab of low density electrically conductive backfill material 16 such as an organic or inorganic carbon aerogel or carbon xerogel is bonded to a piezoelectric ceramic material 12 and to two matching layers 18. The carbon aerogel or xerogel backfill material 16 has a density of 0.02–0.2 $gm.cm^{-3}$ and an acoustic impedance that is substantially less than 1.0 MRayl and an acoustic impedance in the illustrative embodiment that is less than 0.5 MRayl, preferably between 0.01–0.4 MRayls.

Next, in FIG. 11B, the electronic layer 42 is bonded to the carbon aerogel or carbon xerogel backfill material 16 on the side opposite the piezoelectric ceramic material 12 and the matching layers 18. After the electronic layer has been bonded, a plurality of isolation cuts 40 are cut through the matching layers 18, the piezoelectric ceramic material 12, and the backfill material 16 by a laser or a dicing saw to form an array of electrically and acoustically isolated individual elements in FIG. 11C.

Figure 12:
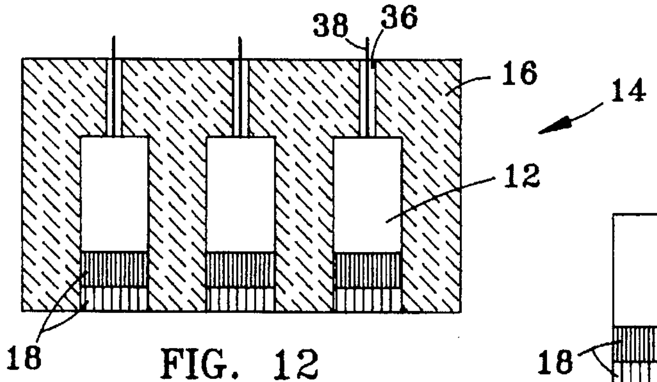
FIG. 12 is a schematic showing the ultrasonic phased array transducer in a fourth embodiment.

A fourth embodiment of the ultrasonic phased array transducer is shown in the schematic of FIG. 12. The fourth embodiment includes the piezoelectric ceramic material 12 and the plurality of matching layers 18 bonded to each other. The piezoelectric ceramic material and the plurality of matching layers are cut therethrough to form an array of electrically and acoustically isolated individual elements. The low density backfill material 16 is made from either an aerogel or an xerogel having an ultralow acoustic impedance and is deposited over the array of electrically and acoustically isolated individual elements. A plurality of the interconnect vias 36 are formed in the backfill material 16 and each have the conducting material 38 deposited therein. In addition, the ultrasonic phased array transducer 14 may include solder pads patterned on the backfill 16 for connecting various types of electronics such as cables, flexible circuit boards, or integrated circuits.

Figure 13A:
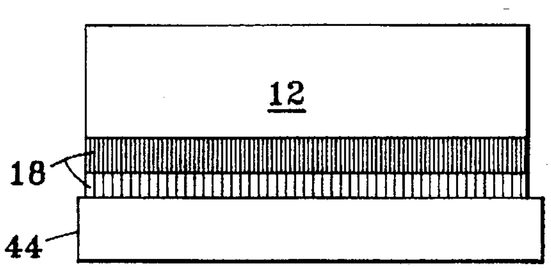
FIGS. 13A–13E illustrate a schematic method of forming the ultrasonic phased array transducer according to the fourth embodiment.
Figure 13B:
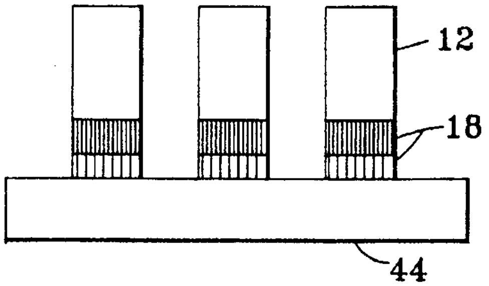
Figure 13C:
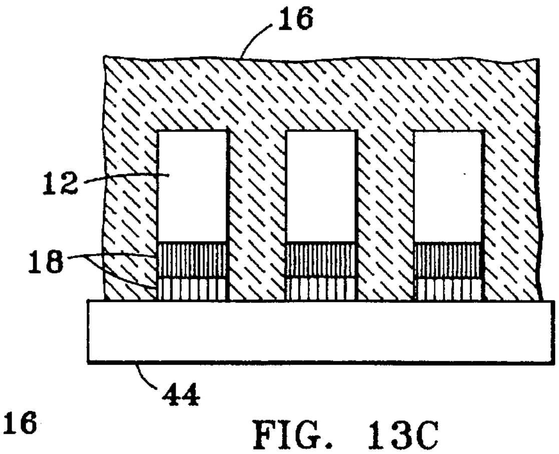
Figure 13D:
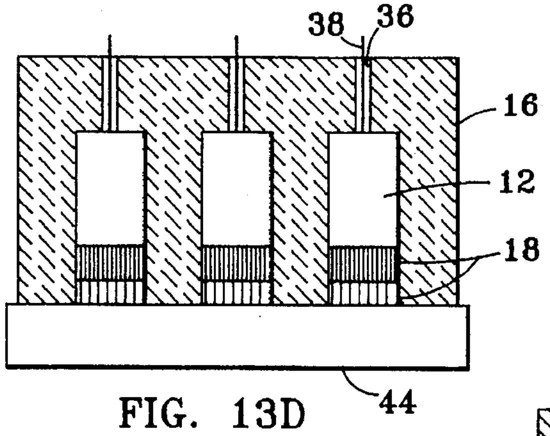
Figure 13E:
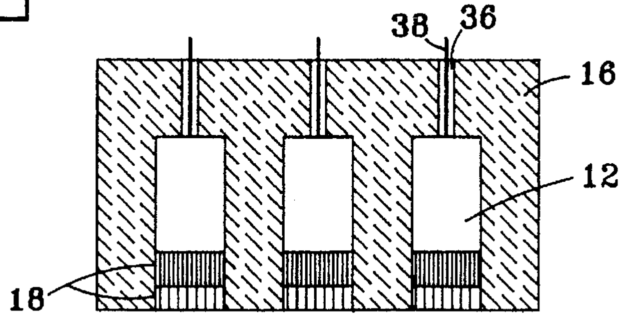

FIGS. 13A–13E illustrate a schematic method of forming the ultrasonic phased array transducer according to the fourth embodiment. The specific processing conditions and dimensions serve to illustrate the present method but can be varied depending upon the materials used and the desired application and geometry of the phased array transducer. First, as shown in FIG. 13A, the piezoelectric ceramic material 12 and the plurality of matching layers 18 are bonded on a substrate 44. The bonded matching layers and the piezoelectric ceramic material are cut in FIG. 13B to form an array of electrically and acoustically isolated individual elements. Next, in FIG. 13C, the low density backfill material 16 made from an organic or inorganic aerogel or xerogel is deposited over the piezoelectric ceramic material 12 and the two matching layers 18. The aerogel or xerogel backfill material 16 has a density of 0.02–0.2 $gm.cm^{-3}$ and an acoustic impedance that is substantially less than 1.0 MRayl and an acoustic impedance in the illustrative embodiment that is less than 0.5 MRayl, preferably between 0.01–0.4 MRayls. Once the aerogel or xerogel backfill material 16 has been deposited over the piezoelectric ceramic material 12 and the matching layers 18 at a depth of a few millimeters, the bonded structure is then planarized. In FIG. 13D, a plurality of interconnect vias 36 are formed in the backfill material 16 by laser machining and the conducting material 38 is deposited in each of the vias. After the conducting material has been deposited, the substrate 44 is then removed.

It is therefore apparent that there has been provided in accordance with the present invention, an ultrasonic phased array transducer having an ultralow backfill and a method for making that fully satisfy the aims and advantages and objectives hereinbefore set forth. The invention has been described with reference to several embodiments, however, it will be appreciated that variations and modifications can be effected by a person of ordinary skill in the art without departing from the scope of the invention.

We claim:

1. A method for forming an ultrasonic phased array transducer with an ultralow impedance backing, the method comprising the steps of:

providing a low density backfill material having an ultralow acoustic impedance, wherein the backfill material is a xerogel;

bonding a piezoelectric ceramic material and a plurality of matching layers to the backfill material; and cutting through portions of the bonded plurality of matching layers, the piezoelectric ceramic material, and the backfill material to form an array of electrically and acoustically isolated individual elements.

2. A method according to claim 1, wherein the backfill material has an acoustic impedance substantially less than 1 MRayl.

3. A method according to claim 2, wherein the backfill material has an acoustic impedance less than 0.5 MRayl.

4. A method according to claim 1, further comprising the step of placing a flexible circuit board between the piezoelectric ceramic material and the ultralow impedance backfill.

5. A method according to claim 1, wherein the bonded plurality of matching layers, the piezoelectric ceramic material, and the backfill material are cut with a laser.

6. A method according to claim 1, wherein the backfill material has a density ranging from 0.02–0.2 $gm.cm^{-3}$.

7. A method for forming an ultrasonic phased array transducer with an ultralow impedance backing, the method comprising the steps of:

providing a low density backfill material having an ultralow acoustic impedance, wherein the backfill material is a xerogel;

bonding a flexible circuit board at one end of the ultralow impedance backfill;

bonding a piezoelectric ceramic material and a plurality of matching layers to the flexible circuit board and the backfill material, wherein the flexible circuit board is bonded between the backfill material and the piezoelectric ceramic material; and cutting through portions of the bonded plurality of matching layers, the piezoelectric ceramic material, the flexible circuit board, and the backfill material to form an array of electrically and acoustically isolated individual elements.

8. A method according to claim 7, wherein the backfill material has an acoustic impedance substantially less than 1 MRayl.

9. A method according to claim 8, wherein the backfill material has an acoustic impedance less than 0.5 MRayl.

10. A method according to claim 7, wherein the backfill material has a density ranging from 0.02–0.2 $gm.cm^{-3}$.

11. An ultrasonic phased array transducer, comprising:

a low density backfill material having an ultralow acoustic impedance, wherein the backfill material is a xerogel; a piezoelectric ceramic material; and a plurality of matching layers; the piezoelectric ceramic material and the plurality of matching layers bonded to the backfill material, a portion of the bonded plurality of matching layers, the piezoelectric ceramic material, and the backfill material having cuts therethrough to form an array of electrically and acoustically isolated individual elements.

12. An ultrasonic phased array transducer according to claim 11, wherein the backfill material has an acoustic impedance substantially less than 1 MRayl.

13. An ultrasonic phased array transducer according to claim 12, wherein the backfill material has an acoustic impedance less than 0.5 MRayl.

14. An ultrasonic phased array transducer according to claim 11, further comprising a flexible circuit board placed between the piezoelectric ceramic material and the ultralow impedance backfill.

15. An ultrasonic phased array transducer according to claim 11, wherein the backfill material has a density ranging from 0.02–0.2 $gm.cm^{-3}$.

16. An ultrasonic phased array transducer, comprising:

a low density backfill material having an ultralow acoustic impedance, wherein the backfill material is a xerogel; a flexible circuit board bonded to one side of the ultralow impedance backfill; a piezoelectric ceramic material; and a plurality of matching layers; the piezoelectric ceramic material and the plurality of matching layers bonded to the flexible circuit board and the backfill material, wherein the flexible circuit board is placed between the piezoelectric ceramic material and the backfill material, a portion of the bonded plurality of matching layers, the piezoelectric ceramic material, the flexible circuit board and the backfill material having cuts therethrough to form an array of electrically and acoustically isolated individual elements.

17. An ultrasonic phased array transducer according to claim 16, wherein the backfill material has an acoustic impedance substantially less than 1 MRayl.

18. An ultrasonic phased array transducer according to claim 17, wherein the backfill material has an acoustic impedance less than 0.5 MRayl.

19. An ultrasonic phased array transducer according to claim 16, wherein the backfill material has a density ranging from 0.02–0.2 $gm.cm^{-3}$.

* * * * *